United States Patent [19]

Clemence et al.

[11] Patent Number: 4,530,932
[45] Date of Patent: Jul. 23, 1985

[54] 4-(1H-INDOL-3-YL)-α-METHYL-PIPERIDINE-1-ETHANOL DERIVATIVES

[75] Inventors: Francois Clemence; Neil L. Brown, both of Paris, France

[73] Assignee: Roussel Uclaf, Paris, France

[21] Appl. No.: 536,889

[22] Filed: Sep. 28, 1983

[30] Foreign Application Priority Data

Oct. 5, 1982 [FR] France .................. 82 16669

[51] Int. Cl.³ .................. C07D 401/04; A61K 31/44
[52] U.S. Cl. .................. 514/318; 514/323; 514/333; 514/339; 546/193; 546/201; 546/256; 546/273
[58] Field of Search ............ 546/273, 201, 193, 256; 424/263, 267

[56] References Cited

U.S. PATENT DOCUMENTS

| 4,100,291 | 7/1978 | Clemence et al. | 546/273 |
| 4,224,333 | 9/1980 | Clemence et al. | 546/197 |
| 4,264,599 | 4/1981 | Eichenberger et al. | 546/201 |
| 4,324,790 | 4/1982 | Guillanme et al. | 546/273 |
| 4,344,945 | 8/1982 | Teranishi et al. | 544/92 |
| 4,344,948 | 8/1982 | Takai et al. | 544/250 |

Primary Examiner—Jane T. Fan
Attorney, Agent, or Firm—Charles A. Muserlian

[57] ABSTRACT

Novel 4-(1H-indol-3-yl)-α-methyl-piperidine-1-ethanol derivatives of the formula

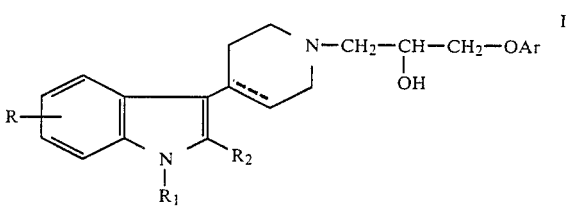

wherein R is selected from the group consisting of hydrogen, halogen, alkyl and alkoxy of 1 to 5 carbon atoms, $-NO_2$, $-NH_2$, $CF_3-$ and $CH_3S-$, $R_1$ is selected from the group consisting of hydrogen and alkyl of 1 to 5 carbon atoms, $R_2$ is selected from the group consisting of hydrogen, alkyl of 1 to 5 carbon atoms and $-OH$, Ar is selected from the group consisting of optionally substituted aryl and heteroaryl, the dotted line indicates the optional presence of a double bond and their non-toxic, pharmaceutically acceptable acid addition salts having remarkable antagonistic properties toward calcium ion and antihypertensive activity and certain compounds possess α and/or β-blocking properties.

24 Claims, No Drawings

4-(1H-INDOL-3-YL)-α-METHYL-PIPERIDINE-1-ETHANOL DERIVATIVES

STATE OF THE ART

Related U.S. patents describing indole compounds are U.S. Pat. Nos. 4,224,333, 4,324,790, 4,344,945 and 4,344,948.

OBJECTS OF THE INVENTION

It is an object of the invention to provide the novel compounds of formula I and their non-toxic, pharmaceutically acceptable acid addition salts and a process for their preparation.

It is another object of the invention to provide novel antihypertensive compositions and a novel method of combatting hypertension in warm-blooded animals.

These and other objects and advantages of the invention will become obvious from the following detailed description.

THE INVENTION

The novel compounds of the invention are selected from the group consisting of 4-(1H-indol-3-yl)-α-methylpiperidine-1-ethanol derivatives of the formula

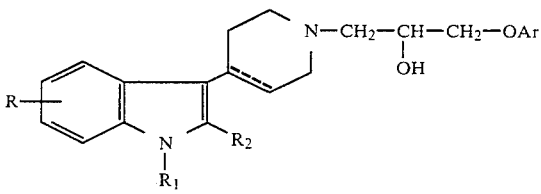

wherein R is selected from the group consisting of hydrogen, halogen, alkyl and alkoxy of 1 to 5 carbon atoms, —$NO_2$, —$NH_2$, $CF_3$— and $CH_3S$—, $R_1$ is selected from the group consisting of hydrogen and alkyl of 1 to 5 carbon atoms, $R_2$ is selected from the group consisting of hydrogen, alkyl of 1 to 5 carbon atoms and —OH, Ar is selected from the group consisting of optionally substituted aryl and heteroaryl of 4 to 14 carbon atoms, the dotted line indicates the optional presence of a double bond and their non-toxic, pharmaceutically acceptable acid addition salts.

Examples of halogens in the compounds of formula I are chlorine and bromine and examples of alkyl of 1 to 5 carbon atoms are methyl, ethyl, n-propyl, isopropyl, n-butyl, tert.-butyl, isobutyl, n-pentyl and isopentyl. Examples of alkoxy of 1 to 5 carbon atoms are methoxy, ethoxy, n-propoxy, isopropoxy, n-butoxy, tert.-butoxy, n-pentoxy and isopentoxy. Examples of aryl are phenyl and naphthyl and examples of heteroaryl are 1H-indol-4-yl, pyridyl, thienyl, thiazolyl and thiadiazolyl.

Examples of suitable substituents on aryl and heteroaryl are halogens such as chlorine, bromine or fluorine; hydroxy; hydroxyalkyl of 1 to 4 carbon atoms such as hydroxymethyl and hydroxybutyl; alkoxy of 1 to 4 carbon atoms such as methoxy, ethoxy and propoxy; alkoxyalkyl of 2 to 7 carbon atoms such as methoxyethyl; carbamoyl; alkenyl and alkenyloxy of 2 to 5 carbon atoms such as propenyl and propenyloxy; acylamino of an organic carboxylic acid of 1 to 7 carbon atoms such as acetamido and butyrylamido; acyl of an alkanoic acid of 1 to 7 carbon atoms such as acetyl; —$NO_2$; —$NH_2$; alkyl of 1 to 4 carbon atoms such as methyl, ethyl and propyl; alkylsulfonamido of 1 to 4 alkyl carbon atoms such as methylsulfonamido; —CN; alkoxycarbonyl of 1 to 4 alkoxy carbon atoms such as methoxycarbonyl; cycloalkyl of 3 to 7 carbon atoms such as cyclohexyl; alkynyl and alkynyloxy of 2 to 6 carbon atoms such as propynyl, ethynyl and propynyloxy; and $CF_3$—.

Examples of suitable acids for the formation of the non-toxic, pharmaceutically acceptable acid addition salts are mineral acids such as hydrochloric acid, hydrobromic acid, nitric acid, sulfuric acid and phosphoric acid and organic acids such as acetic acid, propionic acid, formic acid, benzoic acid, maleic acid, fumaric acid, succinic acid, tartaric acid, citric acid, oxalic acid, glyoxylic acid, aspartic acid, alkane sulfonic acids such as methanesulfonic acid and ethanesulfonic acid, arylsulfonic acids such as benzene sulfonic acid and p-toluene sulfonic acid and aryl carboxylic acids.

Among the preferred compounds of formula I are those wherein $R_2$ is hydrogen or alkyl of 1 to 5 carbon atoms, those wherein the dotted line is a carbon-carbon bond and those wherein Ar is optionally substituted phenyl and $R_1$ and $R_2$ are hydrogen and their non-toxic, pharmaceutically acceptable acid addition salts.

Specific preferred compounds of formula I are 4-(6-methoxy-1H-indol-3-yl)-α-[2-(prop-2-enyloxy)-phenoxymethyl]-piperidine-1-ethanol and 4-(1H-indol-3-yl)-α-[2-(prop-2-enyloxy)-phenoxymethyl]-1,2,3,6-tetrahydropyridin-1-ethanol and their non-toxic, pharmaceutically acceptable acid addition salts, especially the hydrochloride salt.

The novel process of the invention for the preparation of the compounds of formula I comprises reacting an indole of the formula

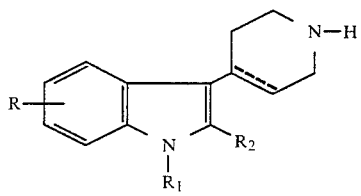

wherein R, $R_1$ and $R_2$ have the above definition with an epoxide of the formula

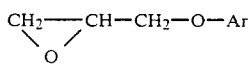

wherein Ar has the above definition to obtain the free base of formula I which may be isolated and optionally salified or subjected to at least one of the following reactions in the appropriate order: removal of any hydroxyl protective groups, reduction of any nitro to amino, acylation of any amino groups and salification with an acid.

In a preferred embodiment of the process of the invention, the reaction of the compounds of formulae II and III is effected in a benzene-methanol mixture at reflux and if Ar contains any hydroxyl groups, they are protected with benzyl derivatives. Removal of the said protective group is effected by reduction with hydrogen in the presence of a catalyst like palladium if the compound does not contain a tetrahydropyridinyl ring. The reduction of nitro groups to amino groups is effected by reduction with hydrogen in the presence of a catalyst such as palladium if the compound does not contain a tetrahydropyridinyl ring and if it does, the reduction is effected by a zinc-acetic acid system. The acylation of any amino groups is effected with a functional acyl derivative such as the acid chloride or acid anhydride.

Since the compounds of formula I have a basic character, the acid addition salts are formed by reacting approximately stoichiometric amounts of the acid and the base with or without isolation of the base.

The novel antihypertensive and calcium ion antagonist compositions of the invention are comprised of an antihypertensively and calcium ion antagonistically effective amount of at least one compound selected from the group consisting of the compounds of formula I and their non-toxic, pharmaceutically acceptable acid addition salts and an inert pharmaceutical carrier or excipient. Some compositions of the invention possess $\alpha$ and/or $\beta$-blocking properties. The compositions may be in the form of tablets, dragees, gelules, granules, suppositories and injectable solutions and suspensions prepared in the usual manner.

Examples of suitable excipients are talc, arabic gum, lactose, starch, magnesium stearate, cocoa butter, aqueous and non-aqueous vehicles, fats of animal and vegetable origin, paraffinic derivatives, glycols, diverse wetting agents, dispersants and emulsifiers and preservatives.

Examples of preferred compositions are those with compounds of formula I wherein $R_2$ is hydrogen or alkyl of 1 to 5 carbon atoms, those wherein the dotted line is a carbon-carbon bond and those wherein Ar is optionally substituted phenyl and $R_1$ and $R_2$ are hydrogen and their non-toxic, pharmaceutically acceptable acid addition salts.

Specific preferred compounds of formula I are 4-(6-methoxy-1H-indol-3-yl)-$\alpha$-[2-(prop-2-enyloxy)-phenoxymethyl]-piperidine-1-ethanol and 4-(1H-indol-3-yl)-$\alpha$-[2-(prop-2-enyloxy)-phenoxymethyl]-1,2,3,6-tetrahydropyridin-1-ethanol and their non-toxic, pharmaceutically acceptable acid addition salts, especially the hydrochloride salt.

The compositions are useful for the treatment of essential arterial hypertension, hypertension of the 50's, menopause, diabetics, obesity and plethoric as well as for the treatment of arterial hypertension caused by age or arteriosclerosis and treatment of hypertension of renal origin. They are also useful for treatment of cardiac insufficiency, angor of all forms and the treatment of arythmia.

The novel method of inducing calcium ion antagonist and antihypertensive activity in warm-blooded animals, including humans, comprises administering to warm-blooded animals an amount of at least one compound of formula I and its non-toxic, pharmaceutically acceptable acid addition salts sufficient to induce antihypertensive and calcium ion antagonistic activity. The compounds may be administered orally, rectally or parenterally. The usual useful daily dosage is depending on the compound, the condition treated and the method of administration. It may be 0.15 to 6.5 mg/kg of the compound of example 1 for treatment of angor in man.

The compounds of formula II are known and may be prepared as described in European patent application Ser. No. 0,022,705. When the compounds to be prepared contain a saturated pyperidyl ring, the corresponding tetrahydropyridinyl compounds can be reduced with hydrogen in the presence of a catalyst such as palladium or diborane. Compounds of formula II with a substituted benzene ring are described in Israel J. Chem., Vol. 4(4) (1966), p. 155–9, J. Org. Chem., Vol. 44(4) (1979), p. 578–586, J. Chem. Soc., (1960), p. 526–533 and J.A.C.S., Vol. 77 (1955), p. 3839–3842, for example. The compounds wherein $R_2$ is —OH may be prepared by the technique of French patent No. 2,420,536.

The products of formula III which are not known may be prepared for example by reaction of a hydroxy aryl of the formula Ar-OH wherein Ar has the above definition with a 1-halo-2,3-epoxy-propane preferably in the presence of a condensation agent such as alkali metal carbonate or bicarbonate. The hydroxy aryls of formula IV are known or can be prepared as indicated in Belgium Pat. No. 640,312 and No. 669,402, Dutch Patent Applications Ser. No. 66-05692 and No. 66-12676, German Pat. No. 1,236,523 and No. 2,106,209, Swiss Pat. No. 469,002 and No. 472,404 and South Africa Pat. No. 68-08345.

In the following examples there are described several preferred embodiments to illustrate the invention. However, it is be understood that the invention is not intended to be limited to the specific embodiments.

EXAMPLE 1

4-(1H-indol-3-yl)-$\alpha$-[{2-(prop-2-enyloxy)-phenoxy}-methyl]-piperidine-1-ethanol hydrochloride A suspension of 5 g of 2-[{2-(prop-2-enyloxy)-phenoxy}-methyl]-oxirane (described in Belgium Pat. No. 669,402), 5 g of 4-(1H-indol-3-yl)-piperidine, 100 ml of anhydrous toluene and 2 drops of methanol was refluxed under an inert atmosphere for 5 hours to form a solution and the toluene was distilled under reduced pressure. The residue was taken up in 250 ml of ether and the mixture was filtered. 3.8 ml of 6.4N hydrogen chloride in ethanol were added to the filtrate and the mixture was stirred for one hour and vacuum filtered. The product was empasted with ether and dried in an oven at 60° C. under reduced pressure. The 10.1 g of product were crystallized from 60 ml of hot acetonitrile, then from ether and dried at 60° C. under reduced pressure to obtain 8 g of 4-(1H-indol-3-yl)-$\alpha$-[{2-(prop-2-enyloxy)-phenoxy}-methyl]-piperidine-1-ethanol hydrochloride melting at 150°–155° C.

Analysis: $C_{25}H_{31}ClN_2O_3$; molecular weight=442.98.
Calculated: %C 67.78, %H 7.05, %Cl 8.00, %N 6.33.
Found: %C 67.9, %H 6.9, %Cl 8.0, %N 6.4.

EXAMPLE 2

4-(1H-indol-3-yl)-$\alpha$-[1-naphthyloxymethyl]-piperidine-1-ethanol

A mixture of 6 g of 4-(1H-indol-3-yl)-$\alpha$-[1-naphthyloxymethyl]-piperidine, 50 ml of benzene and 15 ml of methanol and a solution of 66 g of (1-naphthyloxymethyl)-oxirane [described in J. Med. Chem., Vol. 19, p. 1255] and 40 ml of benzene were admixed with stirring under an inert atmosphere and the mixture was refluxed for 20 hours. 15 ml of methanol were added to the mixture which was refluxed for another 6 hours and was cooled. The mixture was evaporated to dryness under reduced pressure and the residue was empasted with 100 ml of refluxing methanol. The mixture was cooled and vacuum filtered and the product was dried at 80° C. under reduced pressure to obtain 8 g of 4-(1H-indol-3-yl)-$\alpha$-[1-naphthyloxymethyl]-piperidine-1-ethanol melting at $\simeq$185° C.

The said base was dissolved in 200 ml of methylene chloride and 125 ml of methanol and the solution was filtered. 4 ml of 5N hydrogen chloride in ether were added to the filtrate and the mixture was concentrated and was vacuum filtered. The product was washed and dried at 110° C. under reduced pressure to obtain 6.75 g of the hydrochloride of the base melting at ≃240° C.

Analysis: $C_{26}H_{29}ClN_2O_2$; molecular weight=436.98.
Calculated: %C 71.46, %H 6.68, %Cl 8.11, %N 6.41.
Found: %C 71.2, %H 6.9, %Cl 8.2, %N 6.4.

EXAMPLES 3 TO 41

Using the procedure of Example 1 or 2, the appropriate 4-(1H-indol-3-yl)-piperidine and methyloxirane were reacted to obtain the compounds listed in Table I.

TABLE I

| Example | Final Product | Melting point °C. | RF |
|---|---|---|---|
| 3 | 4-(1H—indol-3-yl)-α-[phenoxymethyl]-piperidine-1-ethanol hydrochloride | 252–253° | |
| 4 | 4-(1H—indol-3-yl)-α-[2-cyanophenoxymethyl]-piperidine-1-ethanol hydrochloride | 123° | 0.35 silica (ethyleacetate, CH₃OH, triethylamine 92-5-3) |
| 5 | 4-(1H—indol-3-yl)-α-[4-nitrophenoxymethyl]-piperidine-1-ethanol hydrochloride | 172° | |
| 6 | 4-(1H—indol-3-yl)-α-[2-methoxycarbonyl-phenoxymethyl]-piperidine-1-ethanol hydrochloride | | 0.27 silica (ethylacetate-CH₃OH—triethylamine 92-5-3) |
| 7 | 4-(1H—indol-3-yl)-α-[2-prop-2-enyl)-phenoxymethyl]-piperidine-1-ethanol hydrochloride | 165° | |
| 8 | 4-(1H—indol-3-yl)-α-[4-methoxyphenoxymethyl]-piperidine-1-ethanol hydrochloride | 228° | |
| 9 | 4-(1H—indol-3-yl)-α-[2-methylphenoxymethyl]-piperidine-1-ethanol hydrochloride | 240° (sublimation) | |
| 10 | 4-(1H—indol-3-yl)-α-[2-chlorophenoxymethyl]-piperidine-1-ethanol hydrochloride | 223° | |
| 11 | 4-(1H—indol-3-yl)-α-[2-nitrophenoxymethyl]-piperidine-1-ethanol hydrochloride | 196° | |
| 12 | 4-(1H—indol-3-yl)-α-[2-fluorophenoxymethyl]-piperidine-1-ethanol hydrochloride | 189° | |
| 13 | 4-(1H—indol-3-yl)-α-[2-hydroxy-phenoxymethyl]-piperidine-1-ethanol hydrochloride | 163° | |
| 14 | 4-(1H—indol-3-yl)-α-[2-methoxyphenoxymethyl]-piperidine-1-ethanol hydrochloride | 215° | |
| 15 | 4-(1H—indol-3-yl)-α-[2-cyclohexyl-phenoxymethyl]-piperidine-1-ethanol hydrochloride | 216–218° | |
| 16 | 4-(1H—indol-3-yl)-α-[2-(prop-2-ynyl)-phenoxymethyl]-piperidine-1-ethanol hydrochloride | 124° | |
| 17 | 4-(1H—indol-3-yl)-α-[2-(acetyl-phenoxymethyl]-piperidine-1-ethanol hydrochloride | 200° | |
| 18 | 4-(1H—indol-3-yl)-α-[3-methylphenoxymethyl]-piperidine-1-ethanol hydrochloride | | 0.22 silica (ethylacetate with 1% triethylamine) |
| 19 | 4-(1H—indol-3-yl)-α-[2-amino-phenoxymethyl]-piperidine-1-ethanol fumarate | 220° | |
| 20 | 4-(1H—indol-3-yl)-α-[2-acetamidophenoxymethyl]-piperidine-1-ethanol hydrochloride | 243° | |
| 21 | 4-(1H—indol-3-yl)-α-[4-methylphenoxymethyl]-piperidine-1-ethanol hydrochloride | 216–218° | |
| 22 | 4-(1H—indol-3-yl)-α-[3-chloro-phenoxymethyl]-piperidine-1-ethanol hydrochloride | 226° | |
| 23 | 4-(1H—indol-3-yl)-α-[3-methoxyphenoxymethyl]-piperidine-1-ethanol hydrochloride | 165° | |
| 24 | 4-(1H—indol-3-yl)-α-[2-prop-2-enyloxy)-phenoxymethyl]-1,2,3,6, tetrahydropyridine-1-ethanol fumarate | 176° | |
| 25 | 4-(1H—indol-3-yl)-α-[4-trifluoramethylphenoxymethyl]-piperidine-1-ethanol hydrochloride | 205° | |
| 26 | 4-(1H—indol-3-yl)-α-[4-prop-2-enyloxy)-phenoxymethyl]-piperidine-1-ethanol hydrochloride | 214° | |
| 27 | 4-(1H—indol-3-yl)-α-[3,4-dimethoxyphenoxymethyl]-piperidine-1-ethanol hydrochloride | 206° | |
| 28 | 4-(1H—indol-3-yl)-α-[3-(prop-2-enyloxy)-phenoxymethyl]-piperidine-1-ethanol hydrochloride | 132° | |
| 29 | 4-(1H—indol-3-yl)-α-[3,4-dichlorophenoxymethyl]-piperidine-1-ethanol hydrochloride | 215° | |
| 30 | 4-(1H—indol-3-yl)-α-[3-hydroxyphenoxymethyl]-piperidine-1-ethanol hydrochloride | 160° | |
| 31 | 4-(1-methyl-1H—indol-3-yl)-α-[2-(prop-2-enyloxy)-phenoxymethyl]-piperidine-1-ethanol fumarate | 100° | 0.25 silica (ethylacetate with 1% triethylamine) |
| 32 | 4-(5-methoxy-1H—indol-3-yl)-α-2-(prop-2-enyloxy)-phenoxymethyl]-piperidine-1-ethanol fumarate | | 0.15 silica (ethylacetate with 1% triethylamine) |
| 33 | 4-(6-methoxy-1H—indol-3-yl)-α-[2-(prop-2-enyloxy)-phenoxymethyl]-piperidine-1-ethanol hydrochloride | 147–148° | |
| 34 | 4-[1H—indol-3-yl]-α-[3-(2-methoxycarbonyl)-thienyloxymethyl]-piperidine-1-ethanol hydrochloride | 200° | |
| 35 | 4-[6-chloro-1H—indol-3-yl]-α-[2-(prop-2-enyloxy)-phenoxymethyl]-piperidine-1-ethanol hydrochloride | | |
| 36 | 4-[6-methyl-1H—indol-3-yl]-α-[2-prop-2-enyloxy)-phenoxymethyl]-piperidine-1-ethanol hydrochloride | | |
| 37 | 4-[6-nitro-1H—indol-3-yl]-α-[2-(prop-2-enyloxy)-phenoxymethyl]-piperidine-1-ethanol hydrochloride | | |
| 38 | 4-[6-methylthio-1H—indol-3-yl]-α-[2-(prop-2-enyloxy)-phenoxymethyl]-piperidine-1-ethanol hydrochloride | | |
| 39 | 4-[6-trifluoromethyl-1H—indol-3-yl]-α-[2-(prop-2-enyloxy)-phenoxymethyl]-piperidine-1-ethanol hydrochloride | | |
| 40 | 4-[2-methyl-6-methoxy-1H—indol-3-yl]-α-[2-(prop-2-enyloxy)-phenoxymethyl]-piperidine-1-ethanol hydrochloride | | 0.30 silica (ethylacetate with 1% triethylamine) |
| 41 | Acid fumarate of 4-(2-hydroxy-1H—indol-3-yl]-α-[2-(prop-2-enyloxy)-phenoxymethyl]-piperidine-1-ethanol | 172–174° | |

In Example 13, the hydroxy of 2-hydroxyphenoxymethyl-oxirane was protected with a benzyl which was removed by reduction with hydrogen over palladium in ethyl acetate. In Example 19, the product of Example 11 was reduced with hydrogen over palladium in methanol and was salified with fumaric acid. In Example 20, the base of the product of Example 19 was reacted with acetyl chloride in benzene in the presence of triethylamine followed by treatment with sodium ethoxide and salification with hydrochloric acid. In Example 30, the hydroxy was protected by benzyl which was removed by hydrogenation over palladium in ethyl acetate.

EXAMPLE 42

Cuttable tablets were prepared containing 20 mg of 4-(6-Methoxy-1H-indol-3-yl)-α-[2-(prop-2-enyloxy)-phenoxymethyl]-piperidine-1-ethanol hydrochloride and sufficient excipient of lactose, starch, talc and magnesium stearate for a final tablet weight of 100 mg.

Tablets were prepared containing 75 mg of 4-(1H-indol-3-yl)-α-[2-(prop-2-enyloxy)-phenoxymethyl]-1,2,3,6-tetrahydropyridine-1-ethanol hydrochloride and sufficient excipient of lactose, starch, talc and magnesium stearate for a final weight of 100 mg.

PHARMACOLOGICAL DATA

A. In Vitro anticalcic activity

Rat arteries decoupled in a spiral were attached to a tension collector and were maintained in tanks containing 2.5 ml of Krebs-sodium bicarbonate buffer (NaCl: 120.8 mM, KCl: 5.9 mM, $MgCl_2$: 1.2 mM, $NaH_2PO_4$: 1.2 mM, $NaHCO_3$: 15.5 mM, glucose: 12.6 mM), at 37° C. covered with a 95%-5% oxygen-carbon dioxide mixture. The preparations were depolarized with a buffered solution containing 100 mM of potassium ions (NaCl: 26.7 mM, KCl: 100 mM, $MgCl_2$: 1.2 mM, $NaH_2PO_4$: 1.2 mM, $NaHCO_3$: 15.5 mM, glucose 12.6 mM).

A volume of 25 µl of calcium chloride was added to the mixture in a manner to obtain a range of increasing concentrations of calcium ions from 0.1 to 3.0 mM and the contractions of the artery were measured to obtain a control. The operation with range of calcium ions was repeated every 15 minutes and the preparation was washed 4 times after each range. When a stable response was obtained, the operation with the range of calcium ions was effected in the presence of varying concentrations of test compounds until a stable response was obtained.

The arterial contractions depend on the entry of calcium ions into the cells of smooth muscles and are provoked by depolarization of smooth muscles by potassium ions and by action of noradrenaline freed by presynaptic level. By recommencing the operation with denerved arteries by the action of 6-hydroxy-dopamine, the specific action due to noradrenaline is suppressed. The results are expressed in $CI_{50}$ or the dose of test compound which inhibited by 50% the contractions caused by potassium ions and the results of Table II show that the compounds of the invention possess a strong anticalcium activity.

TABLE II

| Example | $CI_{50}$ in µM |
| --- | --- |
| 1 | 4,0 |
| 2 | 3,5 |
| 3 | 2,5 |
| 4 | 3,5 |
| 5 | 4,5 |
| 6 | 3,0 |
| 7 | 0,32 |
| 8 | 4,2 |
| 9 | 3,8 |

TABLE II-continued

| Example | $CI_{50}$ in µM |
| --- | --- |
| 10 | 2,0 |
| 11 | 4,2 |
| 12 | 3,2 |
| 13 | 4,5 |
| 14 | 11,0 |
| 15 | 5,0 |
| 16 | 1,6 |
| 17 | 6,0 |
| 18 | 2,0 |
| 21 | 1,8 |
| 22 | 1,8 |
| 23 | 2,7 |
| 24 | 0,7 |
| 25 | 1,5 |
| 26 | 1,5 |
| 28 | 2,4 |
| 29 | 2,4 |
| 31 | 3,0 |
| 32 | 1,9 |

B. Antiarythmic action

Male guinea pigs weighing between 450 and 500 g were tracheotomized while anesthesized by intraperitoneal administration of 1.25 mg/kg of urethane and were subjected to artifical respiration of 40 to 50 breaths of 5 ml per minute. Needles were subcutaneously implanted to register an electrocardiogram of the guinea pigs for the signal of D II derivation. The test products were orally administered and one hour later, the jugular vein of the guinea pigs were perfused with 0.5 ml per minute of a solution of 150 γ/ml of K-strophanthine and 0.5 ml per minute of a solution of 5 γ/ml of adrenaline and the number of times of the appearance of cardiac rhythm troubles was noted. The results are expressed in percentage of protection with an oral dose of 10 mg/kg of test product that is to say the percentage of lengthening of the time of appearance of cardiac rhythm troubles as compared to the controls. The results of Table III show that the compounds of the invention generally show a good antiarythmic activity.

TABLE III

| Example | Percentage of protection |
| --- | --- |
| 1 | 63 |
| 3 | 55 |
| 4 | 148 |
| 5 | 82 |
| 6 | 37 |
| 7 | 50 |
| 8 | 57 |
| 9 | 48 |
| 10 | 59 |
| 11 | 56 |
| 12 | 90 |
| 13 | 112 |
| 14 | 83 |
| 16 | 71 |
| 17 | 142 |
| 18 | 23 |
| 19 | 165 |
| 21 | 60 |
| 23 | 73 |
| 25 | 35 |
| 26 | 68 |
| 27 | 115 |
| 28 | 103 |
| 29 | 53 |
| 30 | 86 |
| 31 | 49 |
| 32 | 20 |

C. Hypotensive Activity

The hypotensive activity was studied on male rats of the Wistar strain weighing about 300 g and anesthesized with 50 mg/kg of nembutal intraveinously. The test products were administered intraveinously by the jugular vein and the carotidien arterial pressure was measured before and after administration of the test compounds. The variations expressed in percentage of arterial pressure after administration with respect to the initial pressure is reported in Table IV.

TABLE IV

| Product of Example | Dose in mg/kg | % Variation of arterial pressure after administration | | | |
|---|---|---|---|---|---|
| | | 1 minute | 5 minutes | 10 minutes | 30 minutes |
| 4 | 1 | −24 | −21 | −22 | −26 |
| 6 | 1 | −21 | −13 | −13 | 0 |
| 8 | 1 | −10 | −13 | 0 | −13 |
| 9 | 1 | −21 | −9 | −25 | −20 |
| 10 | 1 | −21 | −20 | −12 | −20 |
| 11 | 0,1 | −3 | −7 | −12 | −16 |
| 12 | 1 | −27 | −14 | −27 | −24 |
| 16 | 0,1 | −3 | −6 | −9 | −20 |
| 17 | 1 | −17 | −5 | −18 | −6 |
| 23 | 1 | −7 | −19 | +14 | −17 |
| 24 | 1 | −10 | −16 | −11 | −17 |
| 25 | 1 | −5 | −14 | −6 | −14 |
| 28 | 1 | −5 | −10 | −6 | −9 |

D. Affinity for $\alpha_1$ adrenergic receptors

The test was inspired by that of Mohler et al [Science, Vol. 198 (1977), p. 849-851] and 5 entire brains of male rats weighing an average of 150 g were homogenized in 90 ml of buffer Tris HCl 7.7. After centrifugation at 30,000 g for 15 minutes at 0° to 4° C., the culot was suspended in 240 ml of buffer Tris HCl 50 mM (pH-7.7) and the suspension was centrifuged at 30,000 g for 20 minutes at 0° to 4° C. The new culot was suspended in 480 ml of buffer Krebs Tris HCl (pH of 7.7–50 mM) and 2 ml of the suspension in the presence of 3H prazosine at a concentration of 0.12 mM alone and with increasing concentrations of the test compound or with non-radioactive phentolamine at a concentration of $10^{-5}M$ to determine the non-specific fixation was incubated at 25° C. for 30 minutes.

The incubated suspensions were filtered through Whatman FG/C and the filtered were washed with 3 times with 5 ml of buffer Krebs Tris HCl-pH of 7.7 at 0° to 4° C. The radioactivity of the filters was measured by liquid scintillation and the affinity of the test compound for $\alpha_1$ adrenergic receptors was compared relative to phentolamine as the reference compound by the formula

ARL = 100 × (CB/CX)

CD = concentration of phentolamine inhibiting by 50% the specific fixation of 3H prazosine.
CX = concentration of test product inhibiting by 50% the specific fixation of 3H prazosine.
ARL = relative affinity
The results of Table V show that the compounds of the invention possess a remarkable affinity for $\alpha_1$-adrenergic receptors.

TABLE V

| Product of Example | % Arl |
|---|---|
| 1 | 247 |
| 4 | 145 |
| 5 | 77 |
| 6 | 253 |
| 7 | 100 |

TABLE V-continued

| Product of Example | % Arl |
|---|---|
| 8 | 222 |
| 9 | 92 |
| 11 | 77 |
| 12 | 233 |
| 13 | 293 |
| 16 | 321 |
| 17 | 159 |
| 20 | 311 |
| 21 | 93 |
| 22 | 70 |

E. Affinity for $\beta_1$ adrenergic receptors

The test was inspired by that of Mohler et al [Science, Vol. 198 (1977), p. 849-851] and 10 cortexes removed from the brains of male rats weighing an average of 150 g were homogenized in 90 ml of 0.32M of sucrose. After centrifuging the homogenized mixture at 1000 g for 20 minutes at 0° C., the surnageant was centrifuged at 30,000 g for 15 minutes at 0° to 4° C. The culot was suspended in 120 ml of buffer Tris HCl 50 mM with a pH of 7.7 and was centrifuged at 30,000 g for 15 minutes at 0° to 4° C. The resulting culot was suspended in 480 ml of buffer Krebs Tris HCl (50 mM-pH of 7.7) and 2 ml of the suspension in the presence of 3H dihydroalprenolol at a concentration of $10^{-9}M$ alone and with increasing concentrations of the test compound or with non-radioactive propranolol at a concentration of $10^{-5}M$ to determine the non-specific fixation was incubated at 37° C. for 10 minutes.

The incubated suspensions were filtered through Whatman GF/C and the filters were washed 3 times with 5 ml of buffer Krebs Tris HCl (pH-7.7) at 0° C. The radioactivity of the filters was measured by liquid scintillation and the affinity of the test compounds for $\beta_1$-adrenergic receptors was compared using propranolol as a standard as in Test D. The results are reported in Table VI.

TABLE VI

| Product of Example | ARL in % |
|---|---|
| 1 | 7.3 |
| 2 | 0.9 |
| 4 | 13.3 |
| 6 | 1.3 |
| 7 | 3.7 |
| 9 | 2.55 |
| 10 | 1.95 |
| 11 | 1.2 |
| 12 | 1.2 |
| 13 | 1.1 |
| 16 | 5.8 |
| 17 | 1.2 |

The results of Table VI show that the compounds of the invention have a notable affinity for $\beta_1$-adrenergic receptors.

F. Affinity for $\beta_2$-adrenergic receptors

The technique was inspired by that of Mohler et al [Science, Vol. 198 (1977), p. 849-851] and the cerebellums of male rats weighing an average of 150 g were homogenized in 90 ml of 0.32M sucrose. After centrifugation of the homogenized mixture at 1000 g for 20 minutes at 0° C., the surnageant was centrifuged at 30,000 g for 15 minutes at 0° to 4° C. The culot was suspended in 120 ml of buffer Tris HCl (50 mM-pH of 7.7) and the suspension was centrifuged at 30,000 g for 15 minutes at 0° to 4° C. The resulting culot was suspended in 480 ml of buffer Krebs Tris HCl with a pH of 7.7 and 2 ml of the suspension was incubated at 37° C. for 10 minutes in the presence of 3H dihydroalprenolol at a concentration of $10^{-9}M$ alone and with increasing concentrations of the test compound or with $10^{-5}M$ of non-radioactive propranolol to determine the non-specific fixation.

The incubated suspensions were filtered through Whatman FG/C filter and the filters were rinsed 3 times with 5 ml of buffer Krebs Tris HCl with a pH of 7.7 at 0° C. The radioactivity of the filters was measured by liquid scintillation and the affinity of the test compounds for $\beta_2$-adrenergic receptors relative to propranolol as a standard was determined similar as to Test D. The results are reported in Table VII.

TABLE VII

| Product of Example | ARL in % |
|---|---|
| 1 | 10.5 |
| 4 | 1.1 |
| 6 | 3.5 |
| 7 | 10 |
| 15 | 5.4 |
| 16 | 11 |
| 17 | 3.3 |

The results of Table VII show that the compounds of the invention possess a notable affinity for $\beta_2$-adrenergic activity.

G. Acute toxicity

The $DL_0$ dose or the maximum dose orally administered to mice which did not cause any deaths after 8 days was determined and the results are reported in Table VIII.

TABLE VIII

| Example | $DL_0$ |
|---|---|
| 1 | 100 |
| 2 | >1000 |
| 4 | >100 |
| 5 | >200 |
| 6 | 80 |
| 7 | >200 |
| 8 | >200 |
| 9 | >100 |
| 10 | >100 |
| 11 | 100 |
| 12 | 80 |
| 13 | >100 |
| 14 | >100 |
| 15 | >100 |
| 16 | >100 |
| 17 | >100 |
| 18 | >100 |
| 19 | >100 |
| 21 | >100 |
| 22 | 80 |
| 23 | >200 |
| 24 | >200 |
| 25 | 100 |
| 26 | >200 |
| 27 | 80 |
| 28 | >100 |
| 29 | >100 |
| 30 | >100 |

Various modifications of the products and methods of the invention may be made without departing from the spirit or scope thereof and it is to be understood that the invention is intended to be limited only as defined in the appended claims.

What we claim is:

1. A compound selected from the group consisting of 4-(1H-indol-3-yl)-α-methyl-piperidine-1-ethanol derivatives of the formula

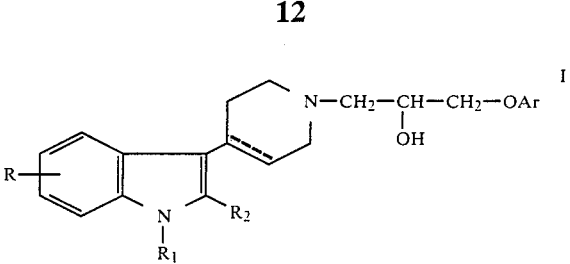

wherein R is selected from the group consisting of hydrogen, halogen, alkyl and alkoxy of 1 to 5 carbon atoms, $-NO_2$, $-NH_2$, $CF_3-$ and $CH_3S-$, $R_1$ is selected from the group consisting of hydrogen and alkyl of 1 to 5 carbon atoms, $R_2$ is selected from the group consisting of hydrogen, alkyl of 1 to 5 carbon atoms and $-OH$, Ar is selected from the group consisting of phenyl, naphthyl, 1H-indol-4-yl, pyridyl, thienyl, thiazolyl and thiadiazolyl optionally substituted with a member of the group consisting of halogen, $-OH$, alkoxy of 1 to 4 carbon atoms hydroxyalkyl of 1 to 4 carbon atoms, alkoxyalkyl of 2 to 7 carbon atoms, carbamoyl, alkenyl and alkenyloxy of 2 to 5 carbon atoms, acylamino of an organic carboxylic acid of 1 to 7 carbon atoms, acyl of an alkanoic acid of 1 to 7 carbon atoms, $-NO_2$, $-NH_2$, alkyl of 1 to 4 carbon atoms, alkylsulfonamido of 1 to 4 alkyl carbon atoms, alkoxycarbonyl of 1 to 4 alkxoy carbon atoms, cycloalkyl of 3 to 7 carbon atoms, $-CF_3$ and alkynyl and alkynyloxy of 2 to 6 carbon atoms, the dotted line indicates the optional presence of a double bond and its non-toxic, pharmaceutically acceptable acid addition salt.

2. A compound of claim 1 wherein $R_2$ is selected from the group consisting of hydrogen and alkyl of 1 to 5 carbon atoms.

3. A compound of claim 1 wherein the dotted line indicates a double bond.

4. A compound of claim 2 wherein the dotted line indicates a double bond.

5. A compound of claim 1 wherein Ar is an optionally substituted phenyl.

6. A compound of claim 1 wherein $R_1$ and $R_2$ are hydrogen.

7. A compound of claim 1 selected from the group consisting of 4-(6-methoxy-1H-indol-3-yl)-α-[2-(prop-2-enyloxy)-phenoxymethyl]-piperidine-1-ethanol and its non-toxic, pharmaceutically acceptable acid addition salt.

8. A compound of claim 1 selected from the group consisting of 4-(1H-indol-3-yl)-α-[2-(prop-2-enyloxy)-phenoxymethyl]-1,2,3,6-tetrahydro-pyridin-1-ethanol and its non-toxic, pharmaceutically acceptable acid addition salt.

9. An antihypertensive and calcium ion antagonistic composition comprising an antihypertensively and calcium ion antagonistically effective amount of at least one compound of claim 1 and a pharmaceutical carrier.

10. A composition of claim 9 wherein $R_2$ is selected from the group consisting of hydrogen and alkyl of 1 to 5 carbon atoms.

11. A composition of claim 9 wherein the dotted line indicates a double bond.

12. A composition of claim 10 wherein the dotted line indicates a double bond.

13. A composition of claim 9 wherein Ar is an optionally substituted phenyl.

14. A composition of claim 9 wherein $R_1$ and $R_2$ are hydrogen.

15. A composition of claim 9 wherein the active compound is selected from the group consisting of 4-(6-methoxy-1H-indol-3-yl)-α-[2-(prop-2-enyloxy)-phenoxymethyl]-piperidine-1-ethanol and its non-toxic, pharmaceutically acceptable acid addition salt.

16. A composition of claim 9 wherein the active compound is selected from the group consisting of 4-(1H-indol-3-yl)-α-[2-(prop-2-enyloxy)-phenoxymethyl]-1,2,3,6-tetrahydropyridin-1-ethanol and its non-toxic, pharmaceutically acceptable acid addition salt.

17. A method of combatting hypertension in warm-blooded animals comprising administering to warm-blooded animals an antihypertensively effective amount of at least one compound of claim 1.

18. A method of claim 17 wherein $R_2$ is selected from the group consisting of hydrogen and alkyl of 1 to 5 carbon atoms.

19. A method of claim 17 wherein the dotted line indicates a double bond.

20. A method of claim 18 wherein the dotted line indicates a double bond.

21. A method of claim 17 wherein Ar is an optionally substituted phenyl.

22. A method of claim 17 wherein $R_1$ and $R_2$ are hydrogen.

23. A method of claim 17 wherein the active compound is selected from the group consisting of 4-(6-methoxy-1H-indol-3-yl)-α-[2-(prop-2-enyloxy)-phenoxymethyl]-piperidine-1-ethanol and its non-toxic, pharmaceutically acceptable acid addition salt.

24. A method of claim 17 wherein the active compound is selected from the group consisting of 4-(1H-indol-3-yl)-α-[2-(prop-2-enyloxy)-phenoxymethyl]-1,2,3,6-tetrahydropyridin-1-ethanol and its non-toxic, pharmaceutically acceptable acid addition salt.

* * * * *